(12) United States Patent
Unger

(10) Patent No.: US 11,451,900 B2
(45) Date of Patent: Sep. 20, 2022

(54) COMMUNICATION DEVICE FOR HEARING PROTECTION DEVICES

(71) Applicant: Good Sportsman Marketing, LLC, Grand Prarie, TX (US)

(72) Inventor: Howard Unger, Henderson, NV (US)

(73) Assignee: Good Sportsman Marketing, LLC, Irving, TX (US)

( * ) Notice: Subject to any disclaimer, the term of this patent is extended or adjusted under 35 U.S.C. 154(b) by 0 days.

(21) Appl. No.: 16/530,722

(22) Filed: Aug. 2, 2019

(65) Prior Publication Data
US 2020/0053451 A1 Feb. 13, 2020

Related U.S. Application Data

(60) Provisional application No. 62/717,809, filed on Aug. 11, 2018.

(51) Int. Cl.
*H04R 1/10* (2006.01)
*H01Q 1/27* (2006.01)
*A61F 11/14* (2006.01)

(52) U.S. Cl.
CPC .......... *H04R 1/1075* (2013.01); *A61F 11/14* (2013.01); *H01Q 1/273* (2013.01); *H04R 1/1008* (2013.01); *H04R 1/1083* (2013.01); *A61F 11/145* (2022.01)

(58) Field of Classification Search
CPC .. H04R 1/1075; H04R 1/1008; H04R 1/1083; H04R 1/1066; H01Q 1/273; A61F 11/14; A61F 2011/145

USPC .................................................. 381/74, 371
See application file for complete search history.

(56) References Cited

U.S. PATENT DOCUMENTS

| | | | | |
|---|---|---|---|---|
| 4,905,322 A * | 3/1990 | Aileo | ..................... | A42B 3/166 181/129 |
| 2009/0323975 A1* | 12/2009 | Groesch | ................. | H04R 5/033 381/71.1 |
| 2014/0321658 A1* | 10/2014 | Rahangdale | ........... | H04R 5/033 381/71.1 |
| 2018/0338201 A1* | 11/2018 | Mann | ....................... | H04R 3/04 |

FOREIGN PATENT DOCUMENTS

WO    WO-2008122081 A * 10/2008 ............... H04R 1/10

* cited by examiner

*Primary Examiner* — Paul Kim
*Assistant Examiner* — Douglas J Suthers
(74) *Attorney, Agent, or Firm* — Lightbulb IP, LLC (57) ABSTRACT

A communication device for hearing protection devices provides communication capabilities to users adorning hearing protection devices, which would ordinarily hinder or block communication. The communication device removably attaches to a cup of a hearing protection device and connects to the speakers thereof. One or more wireless transceivers provide wireless transmission of vocal communication and other sound between users of hearing protection devices enhanced with the communication device. Users remain protected by their hearing protection devices and while communicating freely in high decibel environments.

20 Claims, 4 Drawing Sheets

COMMUNICATION DEVICE FOR HEARING PROTECTION DEVICES

CROSS-REFERENCE TO RELATED APPLICATION

This application claims priority to U.S. Provisional Patent Application No. 62/717,809, filed Aug. 11, 2018.

BACKGROUND OF THE INVENTION

1. Field of the Invention

The invention relates to communication transceivers and in particular to a communication device for hearing protection devices.

2. Related Art

Personal protective equipment, such as earmuffs or earplugs, are recommended for use in environments where people are exposed to harmful or potentially harmful decibel levels. In general, this equipment protects users by providing a barrier which reduces the level of noise or other sounds that is able to reach the users' ears. For instance, sound may be attenuated by covering the entire ear or by an insert placed in the ear canal.

From the discussion that follows, it will become apparent that the present invention addresses the deficiencies associated with the prior art while providing numerous additional advantages and benefits not contemplated or possible with prior art constructions.

SUMMARY OF THE INVENTION

A communication device for hearing protection devices is disclosed herein. As will be described further below, the communication device allows a user to communicate while remaining protected by a hearing protection device that would ordinarily hinder or block audible communication. In this manner, a user can remain protected while also communicating freely with other users even in a high decibel environment. In addition, the communication device enhances communication by permitting users to communicate over extended distances.

Various embodiments of a communication device for hearing protection devices are disclosed herein. In one exemplary embodiment, a communication device for a hearing protection device comprising one or more cups having one or more speakers and an audio input is disclosed. The communication device comprises an enclosure comprising a device mount. The enclosure is removably secured to at least one of the cups via the device mount.

The communication device also includes a microphone that captures audio, a radio transceiver that wirelessly transmits the audio captured by the microphone to a remote user and wirelessly receives one or more wireless signals carrying audio from the remote user, and an audio output that connects to the audio input of the hearing protection device. The audio carried by the wireless signals is transmitted to the speakers via the audio output.

The enclosure may have a back end having an arcuate shape to receive the at least one of the cups. The device mount may comprise one or more hooks that engage at least one of the cups. In addition, the device mount may be removable from the enclosure. The audio output may comprise a connector aligned such that the connector physically connects to the audio input when the communication device is secured to the cups. In some embodiments, the communication device may include its own power source.

In another exemplary embodiment, a communication device for a hearing protection headset comprising one or more speakers and an audio input is disclosed. The communication device comprises a device mount that removably secures the communication device to the hearing protection headset, a microphone that captures audio, and a radio transceiver that wirelessly transmits the audio captured by the microphone and wirelessly receives audio via one or more wireless signals. An audio output connects to the audio input of the hearing protection headset such that the audio from the wireless signals is transmitted to the speakers via the audio output.

An enclosure having an arcuate shape to receive a portion of the hearing protection headset may be provided in some embodiments. The device mount may have one or more hooks that engage the hearing protection headset, such as one or more cups of the hearing protection headset. The device mount may be movable to engage and disengage the hearing protection headset.

The audio output may have a connector that is aligned such that the connector physically connects to the audio input when the communication device is secured to the hearing protection headset. The audio output may comprise a wireless transmitter that connects wirelessly to the audio input as well. Similar to the above embodiment, a power source may be included.

Various methods are disclosed herein as well. For instance, in one exemplary embodiment a method of improving a hearing protection headset comprising one or more speakers, and an audio input is disclosed. The method comprises providing a communication device comprising a device mount that removably secures the communication device to the hearing protection headset, a microphone that captures audio, a radio transceiver that wirelessly transmits the audio captured by the microphone and wirelessly receives audio via one or more wireless signals, and an audio output.

The method also includes engaging the hearing protection headset with the device mount such that the communication device is secured to the hearing protection headset, transmitting the audio from the wireless signals to the speakers of the hearing protection headset via the audio output, and transmitting the audio captured by the microphone wirelessly via the radio transceiver.

The device mount may be disengaged from the hearing protection headset to permit removal of the communication device from the hearing protection headset. In addition, the device mount may comprise one or more hooks that engage the hearing protection headset to secure the communication device to the hearing protection headset, such as by engaging one or more cups of the hearing protection headset.

The audio output may comprise a connector that is aligned such that the connector physically connects to the audio input when the communication device is secured to the hearing protection headset. The audio output may comprise a wireless transmitter that connects wirelessly to the audio input as well.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

DETAILED DESCRIPTION OF THE INVENTION

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

It is often difficult to communicate when hearing protection devices are adorned. Users often resort to raising their voices or partially or completely removing their hearing protection in order to communicate with other people. This is inconvenient and undesirable in terms of hearing protection. Moreover, vocal communication is limited to the range a user's voice or other audible communication can travel.

In general, the communication device herein adds communication capabilities to hearing protection devices. This permits users to communicate with one another while remaining protected from hazardous sound levels. The communication device also enhances communication by extending the range within which users can communicate. Moreover, the communication device is unobtrusive and can be conveniently used during work, outdoor activity, or other physical activity. The communication device will be first described in connection with a hearing protection device, such as shown in FIGS. 1 and 2.

Figure 1:
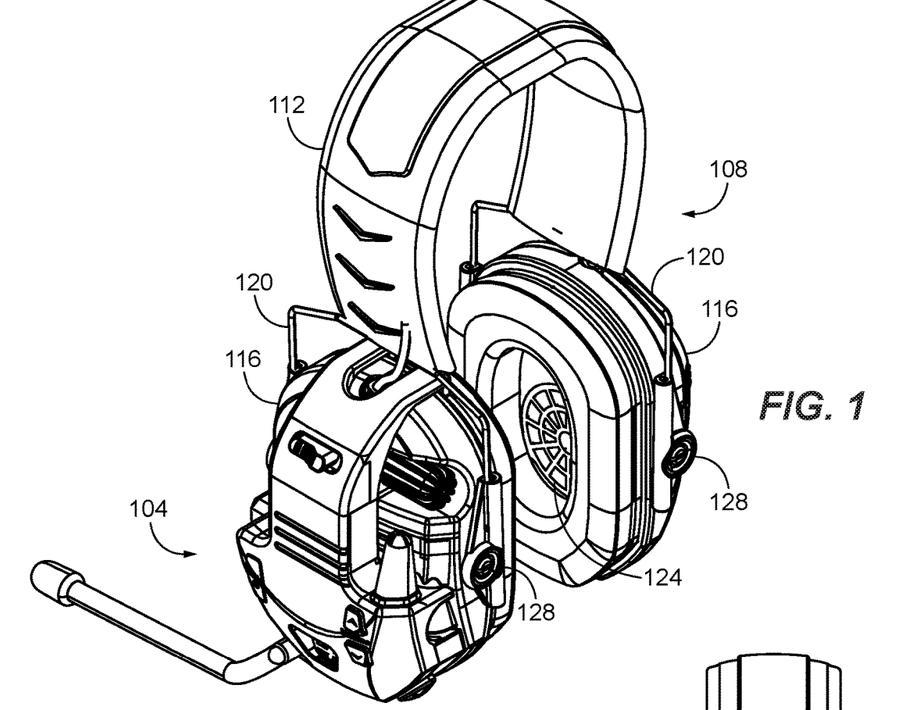
FIG. 1 is a perspective view of an exemplary communication device attached to a hearing protection device.
Figure 2:
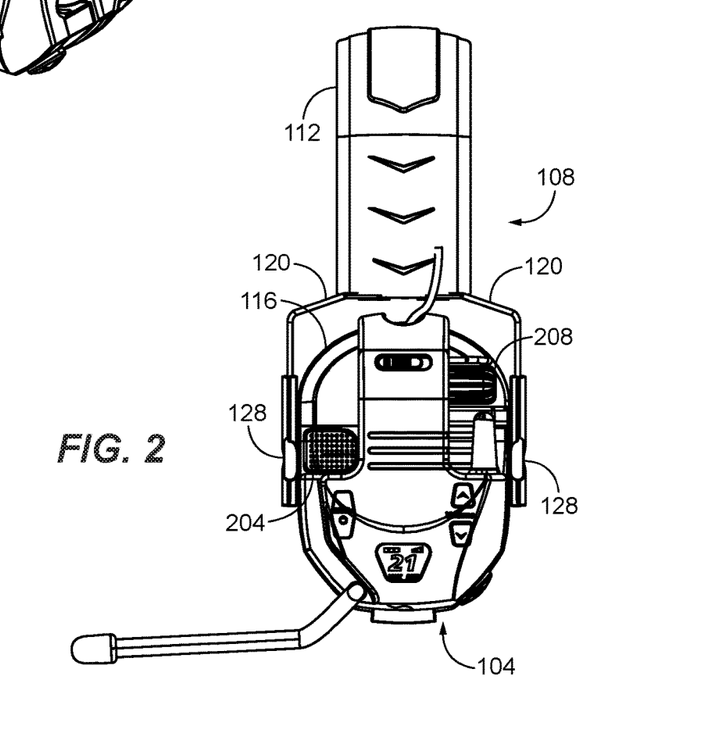
FIG. 2 is a side view of an exemplary communication device attached to a hearing protection device.

FIG. 1 illustrates an exemplary communication device 104, which is an independent device, that has been attached to a hearing protection device 108 for use. As can be seen, a hearing protection device 108 may comprise an earmuff comprising a headband 112 and cups 116 that cover a user's ears. The cups 116 may be pivotally attached to the headband 112 by one or more pivoting mounts 128. In some embodiments, a pivoting mount 128 may comprise one or more arms 120.

The exemplary hearing protection device 108 of FIG. 1 features active noise cancellation via a speaker 124 in each of the cups 112. As shown in FIG. 2, a hearing protection device 108 may comprise one or more microphones 204 for active noise cancellation as well. In addition, one or more controls 208 may be provided, such as to adjust the volume at the speakers 124, turn on/off active noise cancellation, or control other functions of the hearing protection device.

Figures 3, 4:
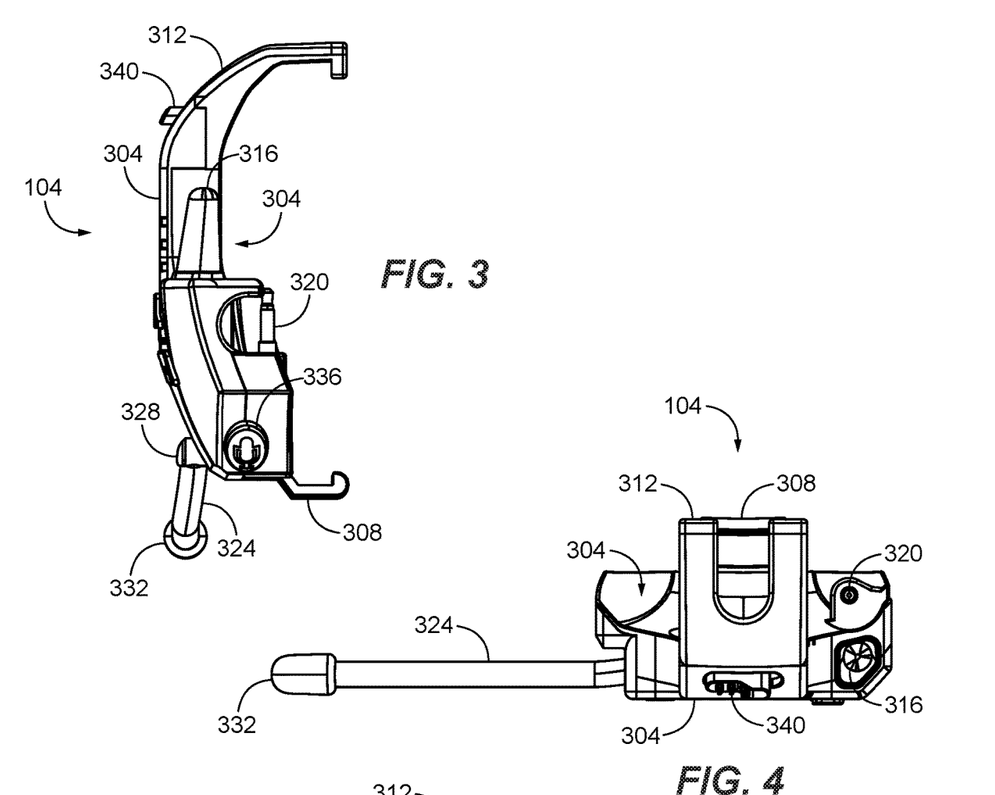
FIG. 3 is a side view of an exemplary communication device.
FIG. 4 is a top view of an exemplary communication device.

FIGS. 3 and 4 respectively illustrate side a top views of an exemplary communication device 104 and components thereof. A communication device 104 may comprise a housing or enclosure 304 that houses or supports various components of the communication device. An enclosure 304 will typically also facilitate removable attachment to a hearing protection device.

For instance, a communication device 104 may comprise one or more device mounts 308, 312 for removably attaching the communication device to a hearing protection device. As can be seen from FIG. 3, a device mount 308, 312 may be shaped to engage a hearing protection device to attach a communication device 104 thereto. In the embodiment of FIG. 3, for instance, the device mounts 308, 312 extend rearward from the enclosure 304 and comprise a projection at their distal ends that engage a cup of a hearing protection device.

A device mount 308, 312 may be a hook or hook shaped, like that shown, or may comprise other structures that facilitate removable attachment to a hearing protection device in one or more embodiments. It is noted that a device mount 308, 312 may be formed of a flexible or resilient material to aid in attachment to and removal from a hearing protection device, while an enclosure 304 remains rigid or at least more rigidly formed. One or more fasteners, such as screws, pins, or the like may be used to secure a communication device 104 in one or more embodiments.

As shown, a first device mount 308 is at a one end of the enclosure 304 while a second device mount is at an opposite end. Specifically, in the embodiment of FIG. 3, the first device mount 308 is at the bottom of the communication device 104 while the second device mount 312 is at the top. In such embodiments, one or more device mounts 308, 312 may engage a peripheral area of a cup to attach a communication device 104 thereto.

In some embodiments, an enclosure 304 may be shaped to receive a cup of a hearing protection device, such as to help secure a communication device 104. A back end of an enclosure 304 may have an arcuate shape, such as to correspond to and receive a cup therein. As shown in FIG. 3 for instance, the back end of the enclosure has a concave shape.

One or more audio output connectors 320 will typically extend outward from an enclosure 304. The audio output connector 320 may provide an electrical, optical, or other type of physical connection through which signals may be transmitted to (or received from) a hearing protection device. In the exemplary embodiment of FIGS. 3 and 4, the audio output connector 320 comprises an electrical connector for communicating audio (or other) signals from the communication device 104 to a hearing protection device.

In one or more embodiments, an enclosure 304 and audio output connector 320 operate in conjunction to automatically connect to a hearing protection device when a communication device 104 is attached to the hearing protection device. Referring to FIG. 3, it can be seen that the enclosure 304 supports the audio output connector 320 at a particular location. This location is selected to align with a corresponding connector of a hearing protection device. In this case, the audio output connector 320 extends upright from a platform at a back end of the enclosure. When attached to a cup, the audio output connector 320 is automatically inserted into the corresponding connector at the cup, thereby allowing communication of audio signals therebetween.

A communication will typically include one or more recording devices, such as one or more microphones 332 to receive a user's voice or other audio. A microphone 332 may be mounted to an enclosure 304. In one or more embodiments, a boom or arm 324 may be provided to position the microphone 332 adjacent a user's mouth or otherwise at a position where the desired audio can be recorded. It is contemplated that a microphone 332 may be movable, such as via mounting on a pivot 328. An arm 324 may also or alternatively be bendable in some embodiments.

One or more antennas 316 will also be typically provided. An antenna 316 aids in transmission and reception of wireless signals to allow communication between multiple communication devices 104. Though shown as a particular antenna 316, it is contemplated that a variety of antennas 316, including internal antennas may be provided. In addition, it is contemplated that one or more antennas 316 may be connected to a communication device 104 via a cable. In this manner, an antenna 316 can be mounted to a hearing protection device or elsewhere, such as to improve signal transmission or reception.

Figure 5:
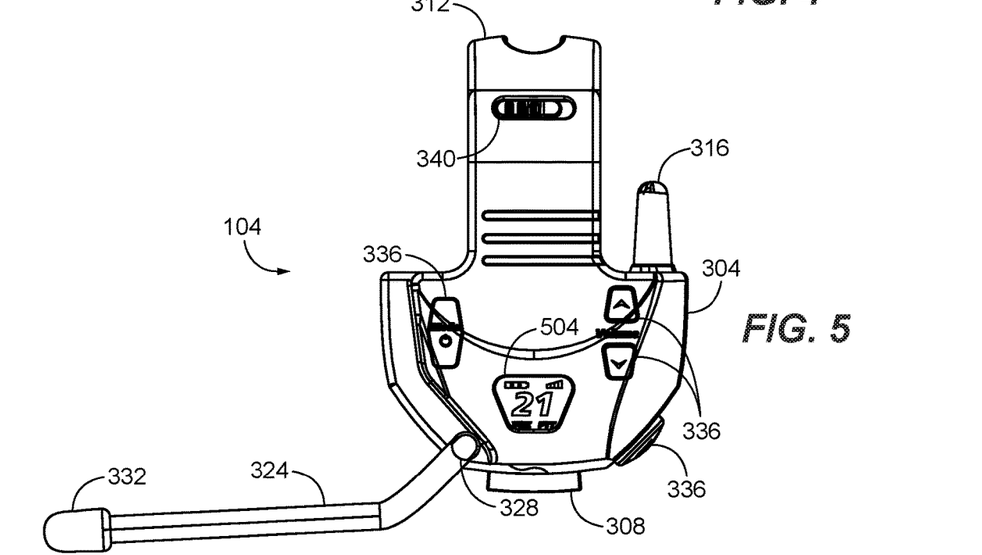
FIG. 5 is a front view of an exemplary communication device.

One or more input devices 336 may be provided to receive user input. To illustrate, an input device 336 may be a button, switch, knob, touch screen, or other user input device. An input device 336 will typically be associated with a particular function. For example, as shown, an input device in the form of a switch 340 is provided to turn the communication device 104 on and off. With reference to FIG. 5, which illustrates a front view of a communication device 104, a plurality of input devices 336 are provided to change channels, raise or lower volume, or activate a push to talk function.

One or more output devices 504 may be provided as well. An output device 504 generally provides feedback to a user. Some exemplary output devices 504 include display screens, vibrators, and speakers for instance. As shown in FIG. 5, the output device 504 comprises a screen that displays battery levels, volume information, and the current communications channel.

Figures 6, 7:
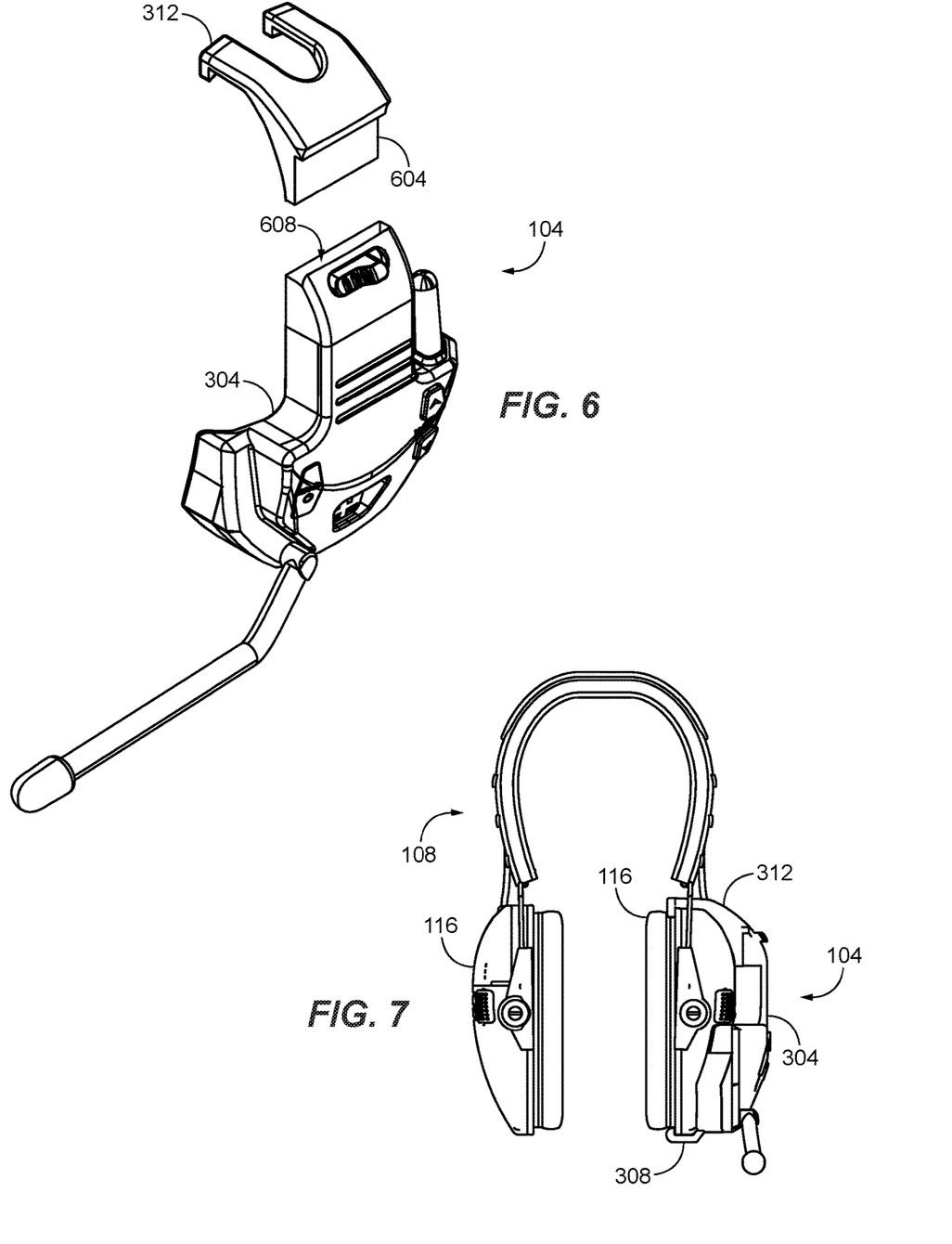
FIG. 6 is a perspective view of an exemplary communication device.
FIG. 7 is a side view of an exemplary communication device attached to a hearing protection device.

FIGS. 6 and 7 illustrate attachment and removal of a communication device 104 relative to a hearing protection device 108. As shown in FIG. 6, one or more device mounts 312 may be removable to facilitate such attachment and removal.

For example, to attach a communication device 104, a first device mount 312 may first be removed, as shown in FIG. 6. The back end of the enclosure 304 may then receive or engage a portion of the hearing protection device 108, such as a cup 116 of the hearing protection device, with a second device mount 308 engaging a structure thereof, such as a lip, edge, or other portion of the cup. The first device mount 312 may then be reattached to the enclosure 304 while engaging the cup as well.

The communication device 104 is attached to the hearing protection device 108 in this manner, as shown in FIG. 7. As can be seen, a projection or hook of the device mounts 308, 312 engage the cup 116 to secure the communication device 104 thereto. As disclosed above, the attachment operation also connects an audio output connector of the communications device 104 to the hearing protection device 108. In this state, the communication device 104 may be considered ready for use.

A device mount 312 may be made removable in various ways. Referring to FIG. 6, a device mount 312 may be removable via a tab or member 604 that is received within a corresponding groove, slot, or compartment 608. It is contemplated that various combinations of mating structures may be provided at the device mount 312 and enclosure 304. In addition, one or more fasteners, such as screws, pins, magnets, or the like, may be used to secure a device mount 312 in a removable fashion. In the embodiment of FIG. 6, a friction fit secures the device mount 312 to the enclosure 304.

Removing a communication device 104 is generally a reverse procedure. In one or more embodiments, for example, one or more device mounts 308, 312 may be disengaged from the hearing protection device 108, and thereafter the communication device 104 may be removed. In the embodiment of FIG. 6, the first device mount 312 may be removed from the enclosure 304, thereby disengaging the first device mount from the hearing protection device's cup 316. Thereafter, the enclosure 304 and the remainder of the communication device 304 can be removed from the hearing protection device 108.

In some embodiments, device mounts 308, 312 need not be removable. As set forth above, a device mount 308, 312 may be flexible or resilient such as to allow malleability during attachment to and removal from a hearing protection device 108. To illustrate, one or more device mounts 308, 312 may be bent or otherwise manipulated when a cup 316 or other portion of a hearing protection device 108 is received or engaged by the enclosure 304 of a communication device 104. A device mount 308, 312 can then be allowed returned to a normal or at rest state to secure a communication device 104 to a hearing protection device 108. Likewise, one or more device mounts 308, 312 can be bent or manipulated to allow a cup 316 to be disengaged from an enclosure 304 when removing the communication device 104 from a hearing protection device 108. It is contemplated that one or more portions of an enclosure may be formed of a resilient material to aid in attachment and removal as well.

Figure 8:
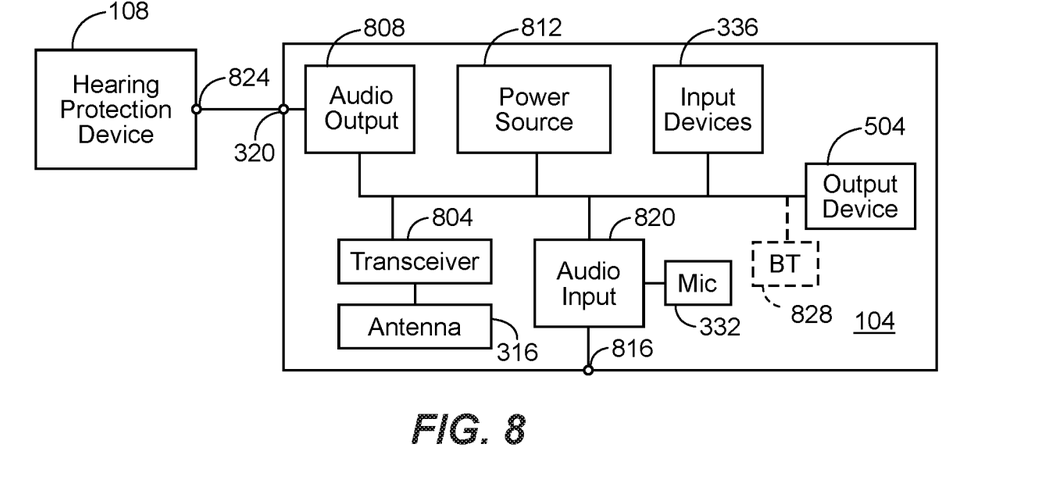
FIG. 8 is a block diagram illustrating components of an exemplary communication device.

FIG. 8 illustrates components of an exemplary communication device 104 that is connected to a hearing protection device 108. Though shown as being connected via a bus, it will be understood that the components may be connected in various ways.

As can be seen, a communication device 104 may comprise one or more radio transceivers 804, one or more power sources 812, one or more audio outputs 808, and one or more audio inputs 820. A power source 812 may comprise one or more batteries, solar panels, generator, or other device that is capable of providing power. A combination of various power sources 812 may be used in some embodiments. Some power sources 812 may be used to charge other power sources. Typically, a power source 812 will be portable, such as a battery.

A radio transceiver 804 may wirelessly transmit audio or other signals, receive such signals, or both. A radio transceiver 804 will typically be connected to one or more antennas 316 and may be capable of communicating wirelessly via one or more communication channels or frequencies, selectable by a user.

It is contemplated that one or more preset sounds or signals may be transmitted by a communication device 104. For example, prerecorded vocalizations, music, sounds, or the like may be transmitted upon engagement of a particular input device 336. A user may select from several preset sounds or signals in some embodiments, via one or more input devices 336. This provides particular information to other users depending on the transmitted sounds or signals, and may be used for entertainment purposes as well. The preset sounds or signals may be recorded or stored on a storage device that is part of or connected to a radio transceiver 804.

Though disclosed above as a radio transceiver 804 capable of transmitting and receiving, it is contemplated that in some embodiments, only a radio transmitter or radio receiver may be provided for one-way or broadcast communication between communication devices 104. In addition, it is contemplated that communication devices 104 need not communicate via radiofrequency transmissions in the various embodiments of the invention. For example, a communication device 104 may communicate optically via lasers, infrared, or other light signals in some embodiments. Accordingly, a variety of transceivers, including optical transceivers, may be utilized.

As disclosed above, a user's vocalizations and other local sounds may be received at an audio input 820. An audio input 820 will generally convert audio or sound into electrical signals, and may receive such audio from one or more microphones 332. An audio input 820 may also or alternatively receive audio from another source via an audio input connector 816.

For example, one or more independent microphones, or the audio output of another device may be connected via an audio input connector 816. A user may play music for instance through a smartphone or portable media player connected to the audio input connector 816. An audio input connector 816 may be an electrical, optical, or other connector. One or more cables may be used to connect external devices to an audio input connector 816.

The audio received at an audio input 820 will typically be transmitted to a radio transceiver 804 for transmission to other communication device 104. This may occur in an automated fashion or when a user engages a push to talk button input device 336 or the like. The same audio may optionally also be outputted via an audio output 808 so that a user can ultimately hear what is being captured or transmitted by their communication device 104.

An audio output 808 generally provides a signal, such as an electrical or optical signal, that can then be outputted to a user in audible form. Typically, an audio output 808 will receive at least the transmissions from a radio transceiver 804. These transmissions include remote audio, which is the transmitted audio from the communication devices 104 of other users. The audio output 808 then provides a corresponding signal to this remote audio as output.

As shown in FIG. 8, this output is received at a hearing protection device 108, when the hearing protection device is connected to the communication device 104. As disclosed above, the connection with a hearing protection device 108 may occur via one or more audio output connectors 320 of the communication device 104 that connect to a corresponding connector 824 of the hearing protection device.

It is contemplated that a length of cable between an audio output connector 320 and an audio output 808 may be provided in some embodiments. This allows a communication device 104 to connect to a wide variety of hearing protection devices 108. It is contemplated that such cable may be retractable in some embodiments.

Though described as an audio input 816 or audio output 808, it is contemplated that either component or both components may function as an input and output device for audio or other signals. For example, control signals for controlling volume or other functionality may be transmitted or received via an audio input 816 or audio output 808. Also, accordingly, an audio input and output may be a single combined component in some embodiments.

It is also contemplated that various wireless connections may be used in addition or instead of the audio input connectors 816 and audio output connectors 320 disclosed above. For example, a BLUETOOTH transceiver or other short-range wireless transceiver 828 may be provided to transmit and receive audio signals. In such embodiments, an audio input 820, audio output 808, or both may be connected to a short-range wireless transceiver 828 thereby reducing or eliminating the need for physical connections with a hearing protection device 108, external microphone, smartphone, or other external device.

As disclosed above, an output device 504 may present communication device status or configuration information, such as battery levels, volume, channel or frequency information, and other information.

Figure 9:
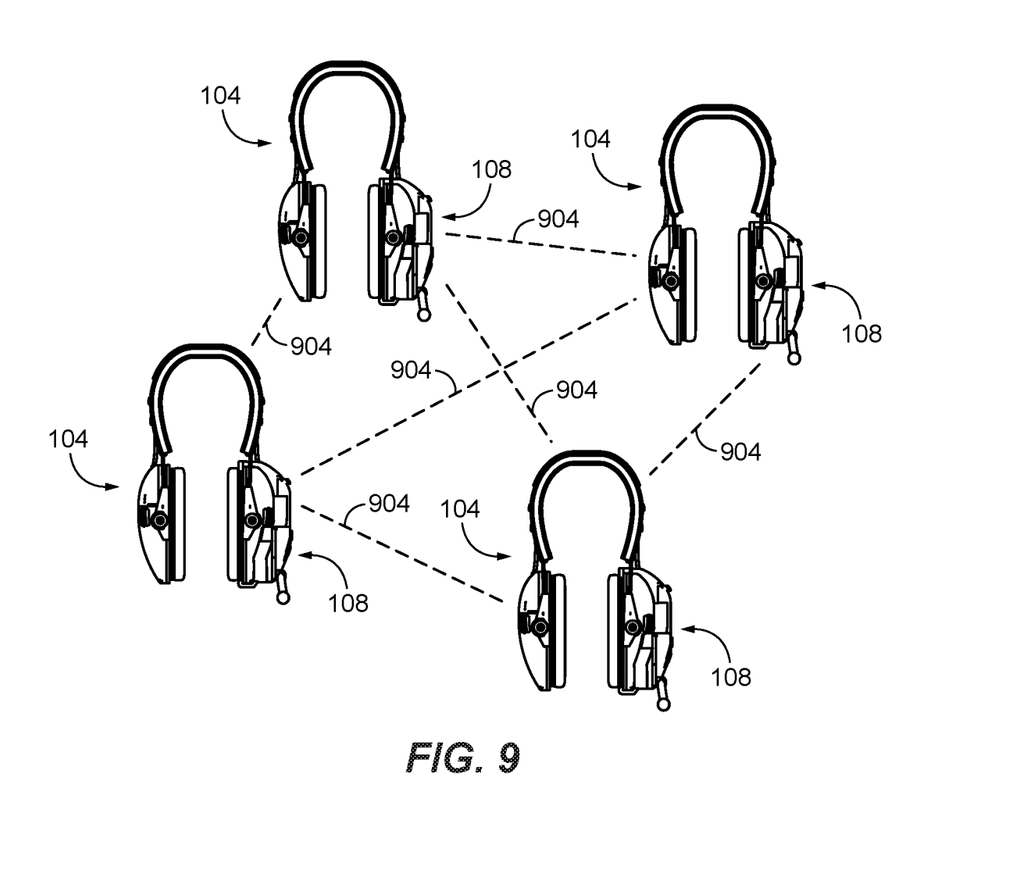
FIG. 9 illustrates exemplary communication devices in operation.

FIG. 9 illustrates a plurality of communication devices 104 in use. As can be seen, each communication device 104 has been attached to a hearing protection device 108. Accordingly, the corresponding users have their hearing protected via active attenuation provided by their hearing protection device 108. This is beneficial in reducing or eliminating the likelihood of hearing damage caused by firearm discharge, industrial noise, or other high decibel sounds. However, the ability for the users to communicate amongst one another is not limited. Instead, the users' ability to communicate is enhanced via the communication devices 104 attached to their hearing protection devices 108. Namely, each user can now communicate wirelessly across a distance while being audible despite the adornment of hearing protection devices by their peers.

As each user speaks, their voice is captured and transmitted from their communication device 104 to other communication devices via one or more wireless connections 904. The receiving communication devices 104 output the user's voice via a speaker of the attached hearing protection device 108. While the hearing protection device 108 is actively attenuating harmful sounds, the output of a communication device 104 is passed through, allowing the same to be heard clearly. It is contemplated that, in some embodiments, an audio output 808 may change or alter the pitch, volume, or other characteristic of audio such that it is not attenuated by a user's particular hearing protection device 108.

As can be seen, the communication device 104 is highly beneficial to users that desire or require hearing protection and the ability to communicate easily without hinderance. This is quite often in hunting, shooting, industrial, or other environments with undesirable sound or noise levels.

While various embodiments of the invention have been described, it will be apparent to those of ordinary skill in the art that many more embodiments and implementations are possible that are within the scope of this invention. In addition, the various features, elements, and embodiments described herein may be claimed or combined in any combination or arrangement.

What is claimed is:

1. A communication device for a hearing protection device, the hearing protection device comprising one or more cups having one or more speakers and an audio input, the communication device comprising:
   an enclosure comprising an outwardly extending member;
   a device mount comprising a first portion formed by a proximal end of the outward extending member and a second portion formed by a distal end of the outward extending member, the second portion of the device mount linearly movable relative to the first portion in a first direction to decrease a dimension of the enclosure and in a second direction to increase the dimension of the enclosure to engage and disengage at least one of the one or more cups; wherein the enclosure is removably secured to the at least one of the one or more cups via the device mount;

a microphone that captures audio;

a radio transceiver that wirelessly transmits the audio captured by the microphone to a remote user and wirelessly receives one or more wireless signals carrying audio from the remote user; and an audio output that connects to the audio input of the hearing protection device, wherein the audio carried by the one or more wireless signals is transmitted to the one or more speakers via the audio output.

2. The communication device of claim 1, wherein the enclosure comprises a back end having an arcuate shape to receive the at least one of the one or more cups.

3. The communication device of claim 1, wherein the device mount comprises one or more hooks that engage the at least one of the one or more cups.

4. The communication device of claim 1, wherein the enclosure comprises a second device mount projecting outward at a position opposed from the device mount, wherein the device mount is a first device mount.

5. The communication device of claim 1, wherein the audio output comprises a connector that is aligned such that the connector physically connects to the audio input when the communication device is secured to the at least one of the one or more cups.

6. The communication device of claim 1, further comprising a power source.

7. The communication device of claim 1, further comprising a second device mount extending from the enclosure at a position opposed from the device mount, wherein the device mount is a first device mount.

8. A communication device for a hearing protection headset, the hearing protection headset comprising one or more speakers and an audio input, the communication device comprising:

a device mount that removably secures the communication device to the hearing protection headset;

a microphone that captures audio;

a radio transceiver that wirelessly transmits the audio captured by the microphone and wirelessly receives audio via one or more wireless signals;

an audio output that connects to the audio input of the hearing protection headset, wherein the audio from the one or more wireless signals is transmitted to the one or more speakers via the audio output; and an enclosure comprising an outwardly extending member, wherein a first portion of the device mount is formed by a proximal end of the outwardly extending member and a second portion of the device mount is formed by a distal end of the outwardly extending member;

wherein the second portion of the device mount is linearly movable relative to the first portion in a first direction to decrease a dimension of the enclosure and in a second direction to increase the dimension of the enclosure to engage and disengage the hearing protection headset to removably secure the communication device to the hearing protection headset.

9. The communication device of claim 8, further comprising an enclosure having an arcuate shape to receive a portion of the hearing protection headset.

10. Communication device of claim 8, wherein the device mount comprises one or more hooks that engage the hearing protection headset.

11. The communication device of claim 8, wherein the device mount comprises one or more hooks that engage one or more cups of the hearing protection headset.

12. The communication device of claim 8, wherein the audio output comprises a connector that is aligned such that the connector physically connects to the audio input when the communication device is secured to the hearing protection headset.

13. The communication device of claim 8, wherein the audio output comprises a wireless transmitter that connects wirelessly to the audio input.

14. The communication device of claim 8, further comprising a power source.

15. A method of improving a hearing protection headset, the hearing protection headset comprising one or more speakers and an audio input, the method comprising:

providing a communication device comprising:

an enclosure comprising an outwardly extending member;

a device mount that removably secures the communication device to the hearing protection headset, the device mount comprising a first portion formed by a proximal end of the outwardly extending member and a second portion formed by a distal end of the outwardly extending member, wherein the second portion is linearly movable relative to the first portion in a first direction to decrease a dimension of the enclosure and in a second direction to increase the dimension of the enclosure to engage and disengage the hearing protection headset;

a microphone that captures audio;

a radio transceiver that wirelessly transmits the audio captured by the microphone and wirelessly receives audio via one or more wireless signals; and an audio output;

transmitting the audio from the one or more wireless signals to the one or more speakers of the hearing protection headset via the audio output; and transmitting the audio captured by the microphone wirelessly via the radio transceiver.

16. The method of claim 15, further comprising moving the second portion of the device mount relative to the first portion to disengage the device mount from the hearing protection headset to permit removal of the communication device from the hearing protection headset.

17. The method of claim 15, wherein the device mount comprises one or more hooks that engage the hearing protection headset to secure the communication device to the hearing protection headset.

18. The method of claim 15, wherein the device mount comprises one or more hooks that engage one or more cups of the hearing protection headset to secure the communication device to the hearing protection headset.

19. The method of claim 15, wherein the audio output comprises a connector that is aligned such that the connector physically connects to the audio input when the communication device is secured to the hearing protection headset.

20. The method of claim 15, wherein the audio output comprises a wireless transmitter that connects wirelessly to the audio input.

* * * * *

UNITED STATES PATENT AND TRADEMARK OFFICE
CERTIFICATE OF CORRECTION

PATENT NO. : 11,451,900 B2  
APPLICATION NO. : 16/530722  
DATED : September 20, 2022  
INVENTOR(S) : Howard Unger

Page 1 of 1

It is certified that error appears in the above-identified patent and that said Letters Patent is hereby corrected as shown below:

In the Claims

Claim 10, Column 10, Line 1, "Communication device" should read --The communication device--.

Signed and Sealed this  
Eighth Day of November, 2022

Katherine Kelly Vidal  
*Director of the United States Patent and Trademark Office*